United States Patent [19]
Wegman et al.

[11] Patent Number: 4,490,559

[45] Date of Patent: Dec. 25, 1984

[54] PROCESS FOR MAKING ALDEHYDES FROM DIESTERS OF CARBONIC ACID

[75] Inventors: Richard W. Wegman, S. Charleston; John B. Letts, Dunbar, both of W. Va.

[73] Assignee: Shell Oil Company, Houston, Tex.

[21] Appl. No.: 593,961

[22] Filed: Mar. 27, 1984

[51] Int. Cl.$^3$ .................... C07C 45/49; C07C 45/41
[52] U.S. Cl. ................................. 568/484; 568/428; 568/435
[58] Field of Search .................... 568/484, 428, 435

[56] References Cited

U.S. PATENT DOCUMENTS

| | | | |
|---|---|---|---|
| 1,023,758 | 4/1912 | Raschig et al. | 568/435 |
| 4,302,611 | 11/1981 | Porcelli | 568/484 |
| 4,447,648 | 5/1984 | Wegman | 568/484 |

Primary Examiner—Natalie Trousof
Assistant Examiner—Bruce D. Gray
Attorney, Agent, or Firm—John M. Duncan

[57] ABSTRACT

Saturated aliphatic aldehydes are prepared by contacting diesters of carbonic acid with synthesis gas and a Group VIII compound, preferably a cobalt compound, a halogen, and optionally a Group V trivalent ligand.

10 Claims, No Drawings

PROCESS FOR MAKING ALDEHYDES FROM DIESTERS OF CARBONIC ACID

BACKGROUND OF THE INVENTION

This invention pertains to a process for making saturated aliphatic aldehydes from diesters of carbonic acid and particularly to the reaction of diesters of carbonic acid with synthesis gas in the presence of a rhodium or cobalt catalyst or other Group VIII transition metal.

Much research work has been done on the conversion of synthesis gas, that is, mixtures of carbon monoxide and hydrogen, into low molecular weight organic compounds. For example, methanol has been made from synthesis gas and then further reacted with synthesis gas by hydroformylation, homologation, or carbonylation to provide acetaldehyde, ethanol and acetic acid, respectively. These reactions are catalyzed by one or more transition metals of Group VIII of the Periodic Table. In these reactions a halogen, as for example, iodine, or halogen containing compounds, for example, methyl iodide, must be utilized in conjunction with the metal catalyst in order for a reaction to be carried out at commercially acceptable rates and selectivities.

It is therefor an object of this invention to provide a process which utilizes synthesis gas and products linear aldehydes at high conversion rates and selectivities under relatively mild reaction conditions.

It is another object of this invention to provide a process for producing linear aldehydes via synthesis gas with a minimum of loss of the starting materials, that is, with high conversions of starting materials to the desired aldehydes.

Other objects will become apparent to those skilled in the art upon a reading of the specifications.

BACKGROUND ART

A general review of the work done on homologation/hydroformylation reactions of acetals is given in Organic Synthesis via Metal Carbonyls, Wiley-Interscience, 1976. Pino et. al. (Chem Ind. 1960 1240) reported the reaction of an orthoester, R—C(OR)$_3$, with synthesis gas and a cobalt catalyst resulting in the formation of a linear aldehyde, alcohol, and ester. In contrast, the reaction of an acetal, R—C(OR)$_2$H, with synthesis gas has been reported to result in the formation of glycol ethers or 2-methoxy aldehydes. For instance, U.S. Pat. No. 2,555,950, (DuPont) claimed a process for the production of 2-methoxy aldehydes and 2-methoxy alkanols from the reaction of synthesis gas with acetals derived from 2 to 3 carbon alkanols. The reaction was carried out at high temperatures (150°–250° C.) and pressures (12,000–22,500 psi) and was catalyzed by cobalt. Only acetals were claimed and the methoxy substituted aldehydes/alcohols were the sole product. Similar chemistry was observed for the reaction of formyls with synthesis gas.

In U.S. Pat. No. 2,429,878 (DuPont), glycol ethers were produced via the reaction of formyls with synthesis gas. The reaction was carried out at high temperatures (100°–350° C.) and pressures (9000–15,000 psi) and was catalyzed by metal form Group VIII of the Periodic Table.

More recently, U.S. Pat. No. 4,062,898 (Ethyl Corporation) claimed a process for the production of linear alcohols by a reaction of acetals (particularly methylal) with synthesis gas. The process was carried out at 150°–250° C. and 500–5,000 psi with a cobalt-ruthenium-iodine catalyst. Little, if any, formation of linear aldehydes were observed in this reaction. Ketals were claimed as a feedstock.

In addition to the above publications, an application entitled "Process For Making Aldehydes From Acetals And Ketals" was filed in the U.S. Patent and Trademark Office on Aug. 31, 1982, Ser. No. 413,466 now U.S. Pat. No. 4,447,648. In this application the acetal or ketal is reacted with synthesis gas at elevated temperature and pressure and in contact with a Group VIII compound as catalyst. There is no disclosure or suggestion, in this commonly assigned application, that aldehydes can be produced from diesters of carbonic acid.

DESCRIPTION OF THE INVENTION

A method of preparing saturated aliphatic aldehydes has now been discovered which comprises contacting diesters of carbonic acid having the formula:

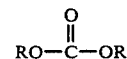

wherein each R is a monovalent radical selected from the class consisting of alkyl radicals having 1 to about 15 carbons, preferably 1 to 3 carbons, aryl radicals having 6 to about 10 ring carbons and cycloalkyl radicals having 5 to about 7 ring carbons, the two R groups need not necessarily be the same, with a catalytic amount of a Group VIII transition metal or compound at a temperature of about 80° C. to about 220° C., preferably 170° C. to 190° C. and a pressure of about 500 to about 6,000 psig preferably about 2,000 to 5,000 psig in the presence of a mixture of carbon monoxide and hydrogen.

The term "catalytic amount of Group VIII compound" is defined to mean one where the mole ratio of Group VIII metal to organic ester of carbonic acid is about 1:5 to about 1:50,000. The preferred amount is a mole ratio of Group VIII metal to organic ester of carbonic acid of about 1:50 to about 1:500. The preferred Group VIII metals are cobalt and rhodium, with cobalt most preferred.

While the preferred Group VIII metals used in the catalysts of this invention are cobalt and rhodium the other members can be used too, viz., iron, nickel, ruthenium, osmium, iridium or platinum.

Illustrative of typical diesters of carbonic acid one may mention the dimethyl, diethyl, diisopropyl, di-n-propyl, dibutyl, diisobutyl, dipentyl, dihexyl, di-2-ethylhexyl and didecyl carbonates; diphenyl carbonate, ditolyl carbonate, dinaphthyl carbonate, dicyclopentyl carbonate, dicyclohexyl carbonate, dicycloheptyl carbonate and the like. The most preferred are dimethyl carbonate and diethyl carbonate.

The catalyst for the invention consists of a Group VIII transition metal, preferably cobalt, a halogen atom, preferably iodine, and optionally a Group V trivalent ligand ER'$_3$ wherein E is preferably nitrogen or phosphorus and R' is an organic moiety.

The cobalt component of the catalyst system can be supplied from any amount of sources, many of which are known to those of ordinary skill in the art. Thus, it is not necessary for an understanding thereof to specifically enumerate every suitable type and specific compound since any of the known compounds can be used. Nevertheless, descriptive of some of the useful cobalt sources are the known cobalt carboxylates such as cobalt formate, cobalt acetate, cobalt benzoate, cobalt toluate, cobalt propionate, cobalt butyrate, cobalt valerate, cobalt hexanoate, cobalt cyclohexanebutyrate, and the like; the cobalt carbonyls such as dicobalt octacarbonyl, acetyl cobalt tetracarbonyl, tricobalt dodecacarabonyl, and the like, including their phosphine substituted analogs many of which are known to those skilled in the art; the cobalt oxides such as cobalt oxide; cobalt hydroxide; cobalt carbonate; and cobalt bicarbonate.

The rhodium component of the catalyst system can be supplied from any number of sources, many of these are known to those of ordinary skill in the art. Thus, it is not necessary for an understanding thereof to specifically enumerate every suitable type and every specific compound since any of the known rhodium compounds can be used.

The rhodium component of the catalyst system of the present invention may be provided by introducing into the reaction zone a compound of rhodium or may be provided by introducing into the reaction zone rhodium. Among the materials which may be charged to the reaction zone to provide the rhodium component of the catalyst system of the present invention are rhodium metal, rhodium salts and oxides, organo rhodium compounds, coordination compounds of rhodium, and the like. Specific examples of materials capable of providing the rhodium constituent of the catalyst system of the present invention may be taken from the following non-limiting partial list of suitable materials.

$RhCl_2$
$RhBr_3$
$RhI_2$
$RhCl_3 \cdot 3H_2O$
$RhBr_3 \cdot 3H_2O$
$Rh_2(CO)_4Cl_2$
$Rh_2(CO)_4Br_2$
$Rh_2(CO)_4I_2$
$Rh_2(CO)_8$
$Rh[(C_6H_5)_3P]_2(CO)I$
$Rh[(C_6H_5)_3P]_2(CO)Cl$
Rh metal
$Rh(NO_3)_3$
$RhCl[(C_6H_5)_3P]_2(CH_3I)_2$
$Rh(SnCl_3)[(C_6H_5)_3P]_2$
$RhCl(CO)[C_4H_5)_3As]_2$
$RhI(CO)[(C_6H_5)_3Sb]_2$
$[(n-C_4H_9)_4N][Rh(CO)_2X_2]$ where X=Cl—, Br—, I—
$[(n-C_4H_9)_4As][Rh(CO)_2X_4]$ where X=Cl—, I—
$[(n-C_4H_9)_4P][Rh(CO)I_4]$
$Rh[(C_6H_5)_3P]_2(CO)Br$
$Rh[(n-C_4H_9)_3P]_2(CO)Br$
$Rh[(n-C_4H_9)_3P]_2(CO)I$
$RhBr[(C_6H_5)_3P]_3$
$RhI [(C_6H_5)_3P]_3$
$RhCl[(C_6H_5)_3P]_2$
$RhCl[(C_6H_5)_3P]_3H_2$
$[(C_6H_5)_3PRh(CO)H$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4Rh_2I_2)_4$ In addition, one can use the other Group VIII transition metals comprising the iron triad, i.e., iron, ruthenium, osmium; the cobalt triad, i.e., cobalt, rhodium, iridium; or the nickel triad, i.e., nickel, palladium, platinum. Though these will catalyze the reaction, the preferred metals are cobalt and rhodium, with the most preferred being cobalt.

When a nitrogen or phosphorus substituted analog or a Group VIII metal halide is used proper adjustment is required to maintain the ratios as they are defined in this invention.

The halide component of the catalyst can be a halogen compound containing iodine, bromine or chlorine or two or more of the same, or the elemental halogen per se, or any mixtures of compounds and/or elements. Their identities are well known to those of ordinary skill in this art. The preferred halogen compound is iodine or inorganic or organic compounds containing the iodine atom. As indicated, the suitable halogen compounds are well known to those of average skill in this art and a complete listing is not necessary for their comprehension. Illustrative thereof one can mention barium iodide, hydriodic acid, cobalt iodide, potassium iodide, lithium iodide, sodium iodide, calcium iodide, ammonium iodide, methyl iodide, ethyl iodide, propyl iodide, 2-ethylhexyl iodide, n-decyl iodide, acetyl iodide, propionyl iodide; the organic ammonium iodides of the formula $R'''_4NI$ and the organic phosphonium iodides of the formula $R'''_4PI$ in which $R'''$ is alkyl, saturated or unsaturated, substituted or unsubstituted, having from 1 to about 10 carbon atoms or aryl, unsubstituted or substituted, having from 6 to 10 ring carbon atoms such as trimethyl ammonium iodide, tetraethyl ammonium iodide, tetra-2-ethylhexyl ammonium iodide, tetraphenyl ammonium iodide, tetramethyl phosphonium iodide, tetrapropylphosphonium iodide, tetra-2-ethylhexyl phosphonium iodide, tetrapropyl phosphonium iodide, tetra-2-ethylhexyl phosphonium iodide, methyltriphenyl phosphonium iodide, and the like; methylammonium iodide, tri-p-tolyl-ammonium iodide, decylammonium iodide, ethylphosphonium iodide, triphenylphosphonium iodide, tricylcohexylphosphonium iodide, tri-p-tolyphosphonium iodide, and the like; also useful are bromine and its corresponding compounds and chlorine and its corresponding compounds. Any source of halogen atom can be used provided that it does not have a deleterious effect on the reaction. Again, one must maintain the defined ratios.

The amount of halogen charged is dependent upon the amount of cobalt or rhodium employed. The halogen: cobalt or rhodium mgm-atom ratio is at least 0.1:1 and can be as high as 20:1. It is preferably from about 0.5:1 to about 10:1 and most preferably from about 1:1 to about 5:1.

Another component of the optional catalyst is a Group V trivalent ligand, $ER'_3$, where E=N, P, As, or Sb and $R'$ is an organic moiety. The preferred $ER'_3$ representatives are $NR'_3$ and $PR'_3$.

The phosphorus component of the catalyst is a trivalent phosphorus compound such as the simple trivalent phosphorus compounds of the formulas $PR'_3$ or $P(OR)_3$ or $R'P(OR_1)_2$ or $R'_2POR'$ or the polydentate trivalent phosphines of the formula $R40_2PC_nH_{2n}RP'_2$, or mixtures thereof, in which $R'$ is an alkyl group, saturated or unsaturated, linear or branched, having from 1 to 20 or more carbon atoms, preferably from 4 to 10 carbon atoms; or an aryl, alkaryl or aralkyl group having from 6 to 10 ring carbon atoms, preferably 6 ring carbon atoms; or cycloalkyl having from 5 to 8 ring carbon atoms, preferably 5 or 6 ring carbon atoms; and n is an integer having a value of from 2 to 8 preferably 2 to 4. The R' groups may be the same or different in the molecule and they can be unsubstituted or substituted with groups which will not unduly interfere with the reaction or have a deleterious effect on it. Mixtures of the phosphorus compounds can be used if one so desires. Though those skilled in the art know the phosphorus compounds, illustrative of suitable compounds one can mention triethylphosphine, tributylphosphine, tri-2-ethylhexylphosphine, triphenylphosphine, tri(4-methoxyphenyl)phosphine, tri-p-tolylphosphine, tri(3-chlorophenyl)phosphine, diphenyl hexylphosphine, dimethyl (3-methoxyphenyl)phosphine, dibutylstearylphosphine, tribenzylphosphine, tricyclohexyphosphine, cyclohexyl dibutylphosphine, propyl diphenylphosphine, dipropyl phenylphosphine, ethyl diproxyphosphine, phenyl diethylphosphine, triethylphosphite, tributylphosphite, tridecyclphosphite, trioctadecylphosphite, triphenylphosphite, tribenzylphosphite, tricyclohexylphosphite, diethylphenylphosphite, methyl diethoxyphosphine, ethyl diethoxyphosphine, butyl dibutoxyphosphine, ethyl dihexoxyphosphine, phenyl diethoxyphosphine, tolyl diethoxyphosphine, diethyl ethoxyphosphine, dibutyl butoxyphosphine, cyclohexyl diethoxyphosphine, diethyl cyclohexoxyphosphine, diethyl phenoxyphosphine, bis(diphenylphosphino)ethane, bis-(diethylphosphino)-propane, bis-(diphenylphosphino)-butane, bis-(diethylphosphino)-octane, and the like.

The trivalent nitrogen compound of the catalyst is an amine of the formula NR'$_3$ or an amide of the formula R"CONR$_2$" in which R' is as previously defined and R" is hydrogen or alkyl, saturated or unsaturated, unsubstituted or substituted having from 1 to about 20 carbon atoms, preferably from 4 to 10 carbon atoms, cycloalkyl, substituted or unsubstituted, having from 5 to 8 ring carbon atoms, or aryl, substituted or unsubstituted, having from 6 to 10 ring carbon atoms. Illustrative thereof are trimethylamine, triethylamine, tri-n-butylamine, tri-t-butylamine, tri-2-ethylhexylamine, methyl dibutylamine, tridodecylamine, tristearylamine, ethyl dibutylamine, tricylcohexylamine, triphenylamine, tri(4-methoxyphenyl)amine, tri(p-chlorophenyl)-amine dibutyl phenylamine, dipentyl cyclopentylamine, ethyl diphenylamine, trinaphthylamine, tri-p-tolylamine, tribenzylamine, tri(3-methylcyclohexyl)amine, formamide, acetamide, chloracetamide, propionamide, benzamide, butylamide, N-methyl formamide, N-methylacetamide, N,N-dimethyl propionamide, N,N-dihexyl butylamide, N,N-dihexyl acetamide, 2-methyl hexylamide, N,N-isobutyl propionamide, N,N-dodecyl nonamide, and the like. Mixtures of the nitrogen compounds or mixtures of nitrogen and phosphorus compounds can be used if desired.

The molar ratio of ER'$_3$ to Co or Rh can vary over a wide range. The preferred range is 50:1 to 1:50 and the most preferred is 10:1 to 1:10.

Although temperatures in the range of about 80°–220° C. can be used in the practice of this invention, it is preferred to use a range of about 170°–190° C.

Pressures of about 200 to about 6,000 psig can be used in the practice of this invention but it is preferred to use a range of about 2,000 to about 5,000 psig.

The ratio of carbon monoxide to hydrogen in the synthesis gas used in this invention can range from about 5:1 to about 1:5 but preferably is in the range of about 2:1 to about 1:2.

Although the claimed method does not require a solvent, one can be used if desired. Exemplary solvents include alkanes having about 5 to about 12 carbons, such as, pentane, hexane, heptane, octane, and the like; saturated aliphatic alcohols having 1 to about 8 carbons, such as methanol, ethanol, propanol, butanol, octanol, and the like; alkyl glycol ethers having 4 to about 12 carbons such as, dimethyl glycol ether, diethyl glycol ether, dimethyl diethylene glycol ether, diethyl diethylene glycol ether, and the like; diaryl ethers having 12 to about 18 carbons such as diphenyl ether, ditolyl ether, and the like.

This invention provides a process that consumes only alcohol and syngas in the formation of aldehyde. The by-products, alcohol and carbon dioxide, of the reaction are recycled back:

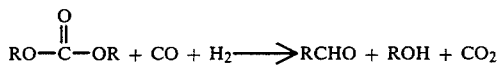

$$RO-\overset{\overset{O}{\|}}{C}-OR + CO + H_2 \longrightarrow RCHO + ROH + CO_2$$

The recycle is carried out by removing the produced aldehyde, RCHO, and replenishing the consumed alcohol, ROH. Formation of carbonate diester by the reaction of CO$_2$ with excess ROH is known technology (for example see Japanese Patent Application 541003012). Regeneration of carbonate diester can be achieved by a two-step process where the ROH and CO$_2$ by-products are removed from the reactor, combined with additional ROH and reacted.

The aldehydes prepared in the practice of this invention are of high enough purity to be used in their conventional role as chemical intermediates, such as, condensation reactions, reduction to alcohols, oxidation to acids, and the like.

The invention is further described in the examples which follow. All parts and percentages are by weight unless otherwise specified.

GENERAL EXPERIMENTAL PROCEDURE

A general procedure as exemplified by the reaction of dimethylcarbonate is as follows: Prior to charging the reactants (catalyst, diluent, and diester of carbonic acid) the autoclave was washed with methanol at 100° C. at a pressure of 400–1,000 psig synthesis gas (CO:H$_2$1:1) for 30 minutes. The reactor was drained, opened, rinsed with acetone, and dried with nitrogen. To the opened and cleaned reactor was charged first the liquid and then the solid reactants. The reactor was closed, purged with synthesis gas, and then pressured to about 1,500 psig with synthesis gas. With agitation (750 rpm), the reactor contents were heated to the prescribed temperature, usually between 120°–200° C. in about 45 minutes. As soon as the temperature had been reached, the reactor was brought to the desired pressure plus 250 psig. The reaction was allowed to consume gas until the pressure had fallen to 250 psig below the desired pressure. The reaction was then repressured. One such cycle was considered 500 psig gas uptake. Unless otherwise specified, reactions were allowed to proceed until 3000 psig gas uptake had occurred.

At the end of an experiment, the reactor contents were normally cooled to 10° C. A vapor phase sample was taken and analyzed for carbon monoxide, hydrogen, carbon dioxide, and methane plus other gaseous hydrocarbons by means of vapor phase chromatography.

The reactor gas phase was vented through two dry-ice acetone traps and then a 2.5 gallon saturated solution of calcium hypochloride to remove iron and/or nickel carbonyls. The reactor was pressurized three times with 90 psig nitrogen and vented through the same trap-vent system.

The reactor contents were dumped into a chilled pressure bottle and crown capped. A Hewlett-Packard Model 5880 gas chromatograph was employed with two columns ⅛"×10', packed with Chromosorb 101 60/80 mesh, which were connected in series with a ⅛" union tube.

EXAMPLE 1

Into a 300 cc autoclave were charged 12 millimoles of $Co(OCOCH_3)_2.4H_2O$ (2.98 g) 12 millimoles of cobalt iodide (3.75g). 24 millimoles of lithium iodide (3.21 g), and 1.78 moles of dimethyl carbonate (160 g). Following the procedure described above, the reactor was heated to 180° C. and the pressure was adjusted to 4,000 psig. The ratio of hydrogen to carbon monoxide was 1:1. The reaction commenced upon pressuring the vessel to 4,000 psig as evidenced by a constant uptake of synthesis gas. The reaction proceeded for approximately 15 minutes after which the reactor was cooled and the product analyzed. The products obtained and their approximate molar amounts are shown in the table. Significant amounts of $CO_2$ were observed in the gas and liquid phases. The actual amounts were not accurately determined. The remainder of the product mixture recovered was unreacted dimethyl carbonate. Under the reaction conditions used the rate to acetaldehyde was 14.6 gram moles/1-hr ($Mhr^{-1}$).

EXAMPLE 2

Example 1 was repeated with the exception that the following conditions and amounts were used:

| $Rh(CO)_2(AcAc)$ | 3.1 g | (12 mm) |
|---|---|---|
| LiI | 4.8 g | (36 mm) |
| Dimethyl Carbonate | 160 g | (1.78 moles) |

The reaction was carried out for 2 hours at 180° C. and 2500 psig. The products and their approximate amounts are shown in the table. Under the conditions utilized the rate to acetaldehyde was 1.1 $Mhr^{-1}$.

EXAMPLE 3

Example 1 was repeated with the exception that the pressure was 5000 psig. The reaction proceeded for approximately 10 minutes. The product distribution was similar to that obtained in Example 1. Under the reaction conditions utilized the rate to acetaldehyde was 20 $Mhr^{-1}$.

EXAMPLE 4

Example 1 was repeated with the exception that the 24 millimoles of lithium iodide was replaced with 24 millimoles of $CaI_2.4H_2O$. The reaction proceeded for approximately 15 minutes. The product distribution was similar to that obtained in Example 1. Under the reaction conditions utilized the rate to acetaldehyde was 12 $Mhr^{-1}$.

EXAMPLE 5

Example 1 was repeated with the exception that the following conditions and amounts were used:

| Cobalt Iodide ($CoI_2$) | = 24 millimoles (7.50 g) |
|---|---|
| Dimethyl carbonate | = 1.78 moles (160 g) |
| Temperature, °C. | = 180 |
| Pressure, psig | = 4000 |
| $H_2/CO$ | = 1.0 |

The reaction proceeded for approximately one hour. The product distribution was similar to that obtained in Example 1. Under the reaction conditions utilized the rate of acetaldehyde was 0.7 $Mhr^{-1}$.

EXAMPLE 6

Example 1 was repeated with the exception that the following conditions and amounts were used:

| $Co(OCOCH_3)_2.4H_2O$ | = 12 millimoles (2.98 g) |
|---|---|
| $CoI_2$ | = 12 millimoles (3.75 g) |
| Dimethyl carbonate | = 1.78 moles (160 g) |
| Temperature, °C. | = 180 |
| Pressure, psig | = 2500 |
| $H_2/CO$ | = 1.0 |

The reaction proceeded for approximately 35 minutes. The product distribution was similar to that obtained in Example 1. Under the reaction conditions utilized the rate to acetaldehyde was 2.2 $Mhr^{-1}$.

EXAMPLE 7

Example 6 was repeated with the exception that the pressure was 1500 psig and 675 psig was consumed in approximately two hours. The product distribution was similar to that obtained in Example 1. Under the reaction conditions utilized the rate to acetaldehyde was 0.5 $Mhr^{-1}$.

The products obtained in Examples 1 to 7 are tabulated below in moles.

TABLE

| Example | 1 | 2 | 3 | 4 | 5 | 6 | 7 |
|---|---|---|---|---|---|---|---|
| Methanol | 0.33 | 0.55 | 0.24 | 0.28 | 0.12 | 0.20 | 0.56 |
| Acetaldehyde* | 0.55 | 0.31 | 0.50 | 0.41 | 0.11 | 0.18 | 0.08 |
| Water | 0.29 | 0.08 | 0.33 | 0.37 | 0.37 | 0.18 | 0.04 |
| Methane | 0.06 | 0.08 | 0.04 | 0.05 | 0.12 | 0.06 | — |
| Ethanol | 0.04 | 0.08 | 0.03 | 0.02 | 0.07 | 0.05 | 0.01 |
| Methyl acetate | 0.03 | 0.17 | 0.03 | 0.02 | 0.01 | — | 0.05 |
| Unknowns ca. | 0.06 | — | 0.06 | 0.04 | 0.05 | 0.04 | 0.04 |

*Includes acetaldehyde equivalents in dimethylacetal.

We claim:

1. Method of preparing saturated aliphatic aldehydes which comprises contacting a diester of carbonic acid having the formula:

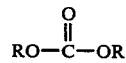

wherein each R is a monovalent radical selected from the class consisting of alkyl having from 1 to 15 carbons, aryl radicals having 6 to about 10 ring carbon and cycloalkyl radicals having 5 to about 7 ring carbons with a catalytic amount of a Group VIII compound and a halogen promoter at a temperature of about 80° to 220° C. and a pressure of about 200 to about 6000 psig in the presence of a mixture of carbon monoxide and hydrogen.

2. Method claimed in claim 1 wherein R is alkyl having 1 to 3 carbons.

3. Method claimed in claim 1 wherein the diester is dimethyl carbonate.

4. Method claimed in claim 1 wherein the temperature is about 170° C. to about 190° C.

5. Method claimed in claim 1 wherein the pressure is about 2000 to about 5000 psig.

6. Method claimed in claim 1 wherein the ratio of carbon monoxide to hydrogen ranges from about 2:1 to about 1:2.

7. Method claimed in claim 1 wherein the mole ratio of Group VIII metal to diester of carbonic acid in the Group VIII compound ranges from about 1:5 to about 1:50000.

8. Method claimed in claim 1 wherein the mole ratio of Group VIII metal to diester of carbonic acid in the Group VIII compound ranges from about 1:50 to about 1:500.

9. Method claimed in claim 1 wherein the Group VIII compound is a cobalt compound.

10. Method claimed in claim 1 wherein a Group V trivalent ligand, $ER'_3$, is present, wherein E is nitrogen or phosphorus and $R'$ is an organic moiety.

* * * * *

UNITED STATES PATENT AND TRADEMARK OFFICE
CERTIFICATE OF CORRECTION

PATENT NO. : 4,490,559

DATED : December 25, 1984

INVENTOR(S) : R. W. Wegman et al.

It is certified that error appears in the above-identified patent and that said Letters Patent is hereby corrected as shown below:

On the title page, "[73] Assignee:"
delete "Shell Oil Company, Houston, Texas" and
substitute therefor --Union Carbide Corporation, Danbury, Conn.--

On the title page, after "Attorney, Agent, or Firm" delete "John M. Duncan" and substitute therefor --F.M. Fazio--.

Signed and Sealed this

Twenty-third Day of April 1985

[SEAL]

Attest:

DONALD J. QUIGG

Attesting Officer

Acting Commissioner of Patents and Trademarks